(12) United States Patent
Puthoff

(10) Patent No.: US 12,251,479 B2
(45) Date of Patent: Mar. 18, 2025

(54) PORTABLE AND WEARABLE DISINFECTING POUCH

(71) Applicant: Joel Puthoff, Charlotte, NC (US)

(72) Inventor: Joel Puthoff, Charlotte, NC (US)

(73) Assignee: Purform LLC, Charlotte, NC (US)

( * ) Notice: Subject to any disclaimer, the term of this patent is extended or adjusted under 35 U.S.C. 154(b) by 846 days.

(21) Appl. No.: 17/477,797

(22) Filed: Sep. 17, 2021

(65) Prior Publication Data

US 2022/0096670 A1 Mar. 31, 2022

Related U.S. Application Data

(60) Provisional application No. 63/083,157, filed on Sep. 25, 2020.

(51) Int. Cl.
*A61L 2/00* (2006.01)
*A45F 3/00* (2006.01)
*A61L 2/18* (2006.01)

(52) U.S. Cl.
CPC ............ *A61L 2/0088* (2013.01); *A45F 3/005* (2013.01); *A61L 2/18* (2013.01); *A61L 2202/122* (2013.01); *A61L 2202/16* (2013.01); *A61L 2202/181* (2013.01)

(58) Field of Classification Search
CPC .... A61L 2/0088; A61L 2/18; A61L 2202/122; A61L 2202/16; A61L 2202/181; A61L 2202/15; A45F 3/005; A45C 11/008
See application file for complete search history.

(56) References Cited

U.S. PATENT DOCUMENTS

| 4,545,414 A * | 10/1985 | Baum | A45C 11/38 |
| --- | --- | --- | --- |
| | | | 224/664 |
| 5,259,541 A * | 11/1993 | Reese | A63B 69/38 |
| | | | 224/663 |
| 5,836,497 A * | 11/1998 | Pelish | A45C 1/04 |
| | | | 224/663 |
| 2002/0134809 A1* | 9/2002 | Angus | A45F 3/12 |
| | | | 224/660 |

(Continued)

FOREIGN PATENT DOCUMENTS

| CN | 204050058 U | 12/2014 |
| --- | --- | --- |
| CN | 204337152 U | 5/2015 |
| JP | 03169238 U | 7/2011 |

OTHER PUBLICATIONS

International Search Report and Written Opinion Issued in corresponding International Application No. PCT/US2021/050797, dated Dec. 27, 2021.

*Primary Examiner* — Sean E Conley
*Assistant Examiner* — Aham Lee
(74) *Attorney, Agent, or Firm* — Jeffrey C. Watson, Esq.; Grell & Watson Patent Attorneys LLC

(57) ABSTRACT

A portable and wearable disinfecting pouch includes a waistbelt and a disinfecting pocket positioned on the waistbelt. The disinfecting pocket includes a first opening, a second opening, and an interior. The first opening is on a first end of the disinfecting pocket. The second opening is on a second end of the disinfecting pocket. The interior is positioned between the first opening and the second opening. A sanitizing pad is positioned in the interior of the disinfecting pocket. The sanitizing pad contains a sanitizing formula configured for disinfecting or sanitizing hands, accessories, or items.

19 Claims, 11 Drawing Sheets

(56) References Cited

U.S. PATENT DOCUMENTS

| | | | | |
|---|---|---|---|---|
| 2006/0078484 A1* | 4/2006 | Greep | ....................... | A61L 2/10 |
| | | | | 250/454.11 |
| 2012/0193386 A1* | 8/2012 | McFarland | ............ | A45C 13/02 |
| | | | | 224/666 |
| 2019/0374009 A1* | 12/2019 | Arikawa | ................. | A45F 3/005 |

* cited by examiner

PORTABLE AND WEARABLE DISINFECTING POUCH

CROSS-REFERENCE TO RELATED APPLICATIONS

This application claims benefit to U.S. Provisional Patent Application No. 63/083,157 filed on Sep. 25, 2020, entitled PORTABLE/WEARABLE DISINFECTING POUCH, which is incorporated by reference in its entirety.

FIELD OF THE DISCLOSURE

The present disclosure is directed to a disinfecting pouch designed to be worn around the waist and used for disinfecting hands and accessories. More specifically, the disclosure is directed to a portable and wearable disinfecting pouch that is configured to disinfect hands and items by placing them inside the pouch and into the disinfecting area.

BACKGROUND

Generally speaking, a wearable pouch is a small fabric pouch worn like a belt around the waist by use of a strap above the hips that is secured usually with some sort of buckle. The straps may have tri-glide slides, or the like, making them adjustable in order to fit properly. It can be considered as a purse worn around the waist. A wearable pouch is also known as a waist bag, fanny pack, belt bag, moon bag, belly bag, or bumbag.

Traditionally the wearable pouch has been worn with the pouch at the front, so people could protect themselves from bandits. Bags attached to belts have been in use since antiquity in many cultures. The modern version may be made from synthetic materials and came into use in the 1980s and they were especially in vogue in the 1990s, but gradually their use fell into decline in the 2000s. Mobile devices (and USB charging cables and backup batteries), bottles of water, snacks, tissue paper, first aid, isopropyl alcohol, contact lenses, and pepper spray are among some of the most common items stored in the bag. Fanny packs designed for concealed carry of a weapon are also available.

In recent times, with the COVID-19 pandemic hitting the world, the need and/or desire to regularly disinfect and/or sanitize one's hands and accessories or items is of utmost importance. The instant disclosure recognizes the difficulty faced to constantly disinfect and/or sanitize one's hands and accessories or items. For example, a waiter, cruise worker, teacher, the like, etc., who's job is to serve their customers or students throughout their shift or school day may make disinfecting and/or sanitizing their hands and accessories or items very difficult, especially on demand or on any type of regular schedule. As such, there is clearly a need and desire to provide a means and/or device to allow people to disinfect and/or sanitize their hands and accessories or items in a convenient and on-demand manner.

The instant disclosure may be designed to address at least certain aspects of the problems or needs discussed above by providing a portable and wearable disinfecting pouch.

SUMMARY

The present disclosure may solve the aforementioned limitations of the currently available disinfecting and/or sanitizing means and/or devices, by providing a portable and wearable disinfecting pouch. The disclosed portable and wearable disinfecting pouch may include a waistbelt with a connector and a disinfecting pocket positioned on the waistbelt. The disinfecting pocket may include a first opening, a second opening, and an interior. The first opening may be on a first end of the disinfecting pocket. The second opening may be on a second end of the disinfecting pocket. The interior may be positioned between the first opening and the second opening. A sanitizing pad may be positioned in the interior of the disinfecting pocket. The sanitizing pad may contain a sanitizing formula configured for disinfecting or sanitizing hands, accessories, or items.

One feature of the disclosed portable and wearable disinfecting pouch may be that it can be designed and configured to be worn around a waist of a user and used for disinfecting the hands, the accessories, or the items.

Another feature of the disclosed portable and wearable disinfecting pouch may be that the hands, the accessories or the items of the user can be sanitized by placing them inside the disinfecting pocket through the first opening, the second opening, or a combination thereof, and onto the sanitizing pad in the interior of the disinfecting pocket.

In select embodiments of the disclosed portable and wearable disinfecting pouch, the disinfecting pocket may include a back portion and a front cover portion. The back portion may be positioned on the waistbelt. The front cover portion may be attached to the back portion on a top side and a bottom side of the disinfecting pocket. In select embodiments, a first elastic band and a second elastic band may be optionally included. The first elastic band may be connected between a first back side of the back portion and a first front side of the front cover portion. The first elastic band may be configured to provide a first elastic opening for the first opening on the first end of the disinfecting pouch. The second elastic band may be connected between a second back side of the back portion and a second front side of the front cover portion. The second elastic band may be configured to provide a second elastic opening for the second opening on the second end of the disinfecting pouch.

Another feature of the disclosed portable and wearable disinfecting pouch may be the inclusion of a removable attachment on the top side of the disinfecting pocket between the front cover portion and the back portion. Wherein, with the removable attachment on the top side of the disinfecting pocket, the interior of the disinfecting pocket may be accessed by disengaging the removable attachment on the top side and folding down the front cover portion. In select embodiments, and clearly not limited thereto, the removable attachment on the top side of the disinfecting pocket may be a zippered attachment. Wherein, the interior of the disinfecting pocket may be accessed by unzipping the zippered attachment on the top side of the disinfecting pocket and folding down the front cover portion.

Another feature of the disclosed portable and wearable disinfecting pouch may be that the disinfecting pocket may further include a drying material. The drying material may be configured for drying the hands, the accessories, or the items. In select embodiments, a divider flap may be positioned between the drying material and the sanitizing pad. The divider flap may be configured to prevent the sanitizing formula on the sanitizing pad from touching the drying material. Whereby, the hands, the accessories or the items of the user can be sanitized by placing them inside the disinfecting pocket through the first opening, the second opening, or a combination thereof, and onto the sanitizing pad in the interior of the disinfecting pocket, and the hands, the accessories or the items of the user can then be dried after they are sanitized by placing them inside the disinfecting pocket through the first opening, the second opening, or the combination thereof, and onto the drying material in the interior of the disinfecting pocket. In select embodiments, the divider flap may include a front side attachment means configured to attach the sanitizing pad to a front side of the divider flap in the interior of the disinfecting pocket. The front side attachment means of the divider flap may include, but is not limited thereto, two vertical strips of a front side hook and loop type fastener configured to removably attach to a back sanitizing side of the sanitizing pad for removably attaching the sanitizing pad to the divider flap. In other select embodiments, the divider flap may include a back side attachment means configured to attach the drying material to a back side of the divider flap in the interior of the disinfecting pocket. The back side attachment means of the divider flap may include, but is not limited to, a center strip of a back side hook and loop type fastener configured to removably attach to a front drying side of the drying material for removably attaching the drying material to the divider flap. In select embodiments, and clearly not limited thereto, the drying material may be configured and sized to be attached to the divider flap in a folded-up orientation for allowing the hands, the accessories, or the items to be inserted into the disinfecting pocket and between the drying material in the folded-up orientation. In select embodiments, the divider flap may be attached to a back portion of the disinfecting pocket on a top side, where the divider flap may be configured to fold upwards and out of the disinfecting pocket when it is opened for removing or attaching the drying material.

In select embodiments of the disclosed portable and wearable disinfecting pouch, the drying material may be, but is not limited to, an antimicrobial fabric cloth. In select embodiments, the antimicrobial fabric cloth may include reinforced edges, like reinforced stitching or the like.

In select embodiments of the disclosed portable and wearable disinfecting pouch, the divider flap may be, but is not limited thereto, a neoprene wall liner.

In select embodiments of the disclosed portable and wearable disinfecting pouch, the sanitizing pad may include, but is not limited thereto, an absorbent foam interior and an antimicrobial fabric exterior. The antimicrobial fabric exterior may surround the absorbent foam interior. In select embodiments, the antimicrobial fabric exterior may include a silver-ion fabric material configured to eliminate growth of bacteria. In select embodiments, the antimicrobial fabric exterior of the sanitizing pad may include at least one filling hole therethrough. Each of the at least one filling holes may be configured for inserting the sanitizing formula inside of the sanitizing pad and onto the absorbent foam interior. In select embodiments, the antimicrobial fabric exterior of the sanitizing pad may include, but is not limited thereto, three of the filling holes. The three filling holes may be positioned along a top edge of the sanitizing pad. The three filling holes may be configured for inserting the sanitizing formula inside of the sanitizing pad and onto the absorbent foam interior in three filling locations.

Another feature of the disclosed portable and wearable disinfecting pouch may be that in select embodiments a front accessories pocket and/or a back accessories pocket may be included. The front accessories pocket may be positioned on the front cover portion of the disinfecting pocket. The back accessories pocket may be positioned on the back portion of the disinfecting pocket. The front accessories pocket and/or the back accessories pocket may be configured for holding accessories or items.

Another feature of the disclosed portable and wearable disinfecting pouch may be that in select embodiments at least one side apron may be included. Each of the at least one side aprons may be positioned along the waistbelt. Each of the at least one side aprons may be configured with slots for holding accessories or items. In select embodiments, and clearly not limited thereto, two side aprons may be included on each side of the disinfecting pouch on the waistbelt.

In another aspect, the instant disclosure embraces the portable and wearable disinfecting pouch in any embodiment and/or combination of embodiments shown and/or described herein.

In another aspect, the instant disclosure embraces a method of disinfecting hands, accessories, or items. The disclosed method of disinfecting hands, accessories, or items may generally include utilizing the disclosed portable and wearable disinfecting pouch in any embodiment and/or combination of embodiments shown and/or described herein. As such, in general, the disclosed method of disinfecting hands, accessories, or items may include providing the disclosed portable and wearable disinfecting pouch in any embodiment and/or combination of embodiments shown and/or described herein. With the provided portable and wearable disinfecting pouch, the disclosed method of disinfecting hands, accessories, or items may further include the steps of: inserting a sanitizing formula into the sanitizing pad, the sanitizing formula is configured for disinfecting or sanitizing the hands, the accessories, or the items; and disinfecting the hands, the accessories, or the items by inserting the hands, the accessories, or the items into the first opening, the second opening, or a combination thereof. into the interior of the disinfecting pocket and onto the sanitizing pad.

In select embodiments of the disclosed method of disinfecting hands, accessories, or items, when the provided portable and wearable disinfecting pouch further includes a drying material inside of the disinfecting pocket, the disclosed method of disinfecting hands, accessories, or items may further include drying the hands, the accessories or the items after they are disinfected by placing them inside the disinfecting pocket through the first opening, the second opening, or the combination thereof, and onto the drying material in the interior of the disinfecting pocket.

The foregoing illustrative summary, as well as other exemplary objectives and/or advantages of the disclosure, and the manner in which the same are accomplished, are further explained within the following detailed description and its accompanying drawings.

BRIEF DESCRIPTION OF THE DRAWINGS

The present disclosure will be better understood by reading the Detailed Description with reference to the accompanying drawings, which are not necessarily drawn to scale, and in which like reference numerals denote similar structure and refer to like elements throughout, and in which.

Figure 1:
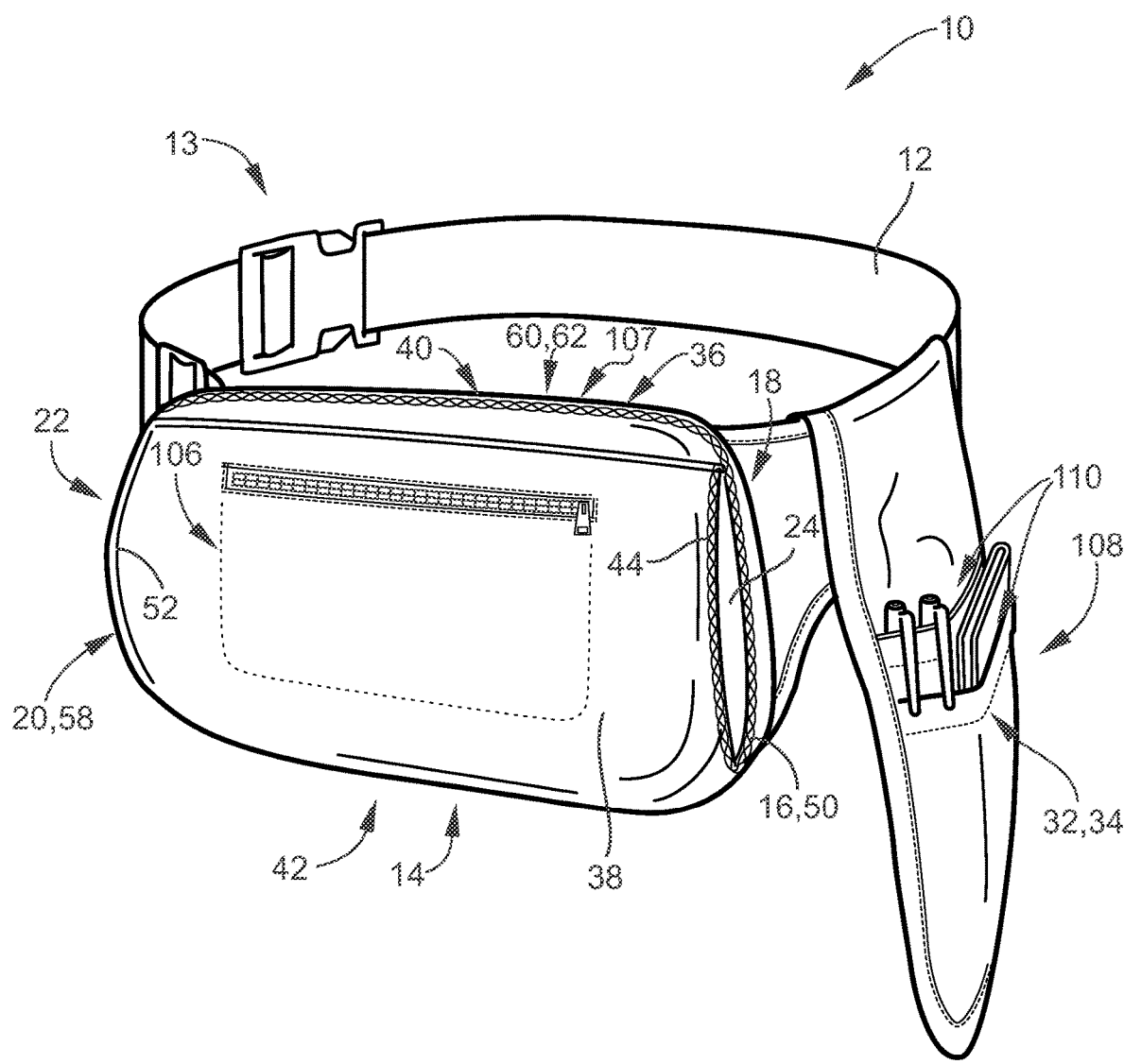
FIG. 1 is a right side, front perspective view of the disclosed portable and wearable disinfecting pouch according to select embodiments of the instant disclosure.

It is to be noted that the drawings presented are intended solely for the purpose of illustration and that they are, therefore, neither desired nor intended to limit the disclosure to any or all of the exact details of construction shown, except insofar as they may be deemed essential to the claimed disclosure.

DETAILED DESCRIPTION

Referring now to FIGS. 1-13, in describing the exemplary embodiments of the present disclosure, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples and are merely examples among other possible examples.

Referring to FIGS. 1-12, the present disclosure may solve the aforementioned limitations of the currently available disinfecting and/or sanitizing means and/or devices by providing portable and wearable disinfecting pouch 10. Applicant notes that the terms disinfecting, sanitizing, or the like, are used interchangeable herein and are generally meant to make clean/hygienic and/or to remove or kill germs and bacteria. Portable and wearable disinfecting pouch 10 may include waistbelt 12 with connector 13. Disinfecting pocket 14 may be positioned on waistbelt 12. Disinfecting pocket 14 may include first opening 16, second opening 20, and interior 24. First opening 16 may be on first end 18 of disinfecting pocket 14. Second opening 20 may be on second end 22 of disinfecting pocket 14. Interior 24 may be positioned between first opening 16 and second opening 20. Sanitizing pad 26 may be positioned in interior 24 of disinfecting pocket 14. Sanitizing pad 26 may contain sanitizing formula 28 configured for disinfecting or sanitizing hands 30, accessories 32, items 34, the like, and/or other desired items to be disinfected, sanitized and/or the like.

Figure 2:
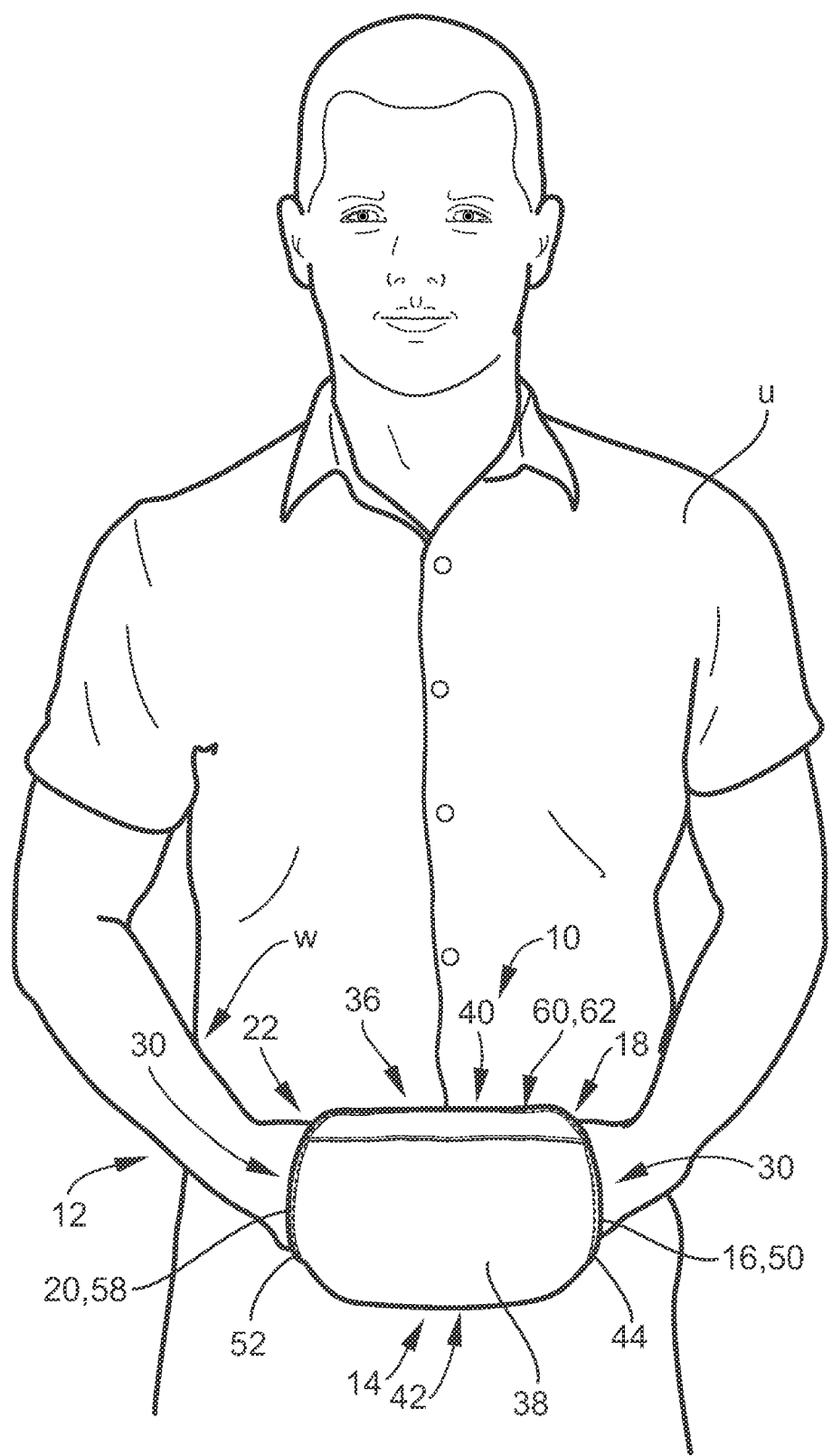
FIG. 2 is a front perspective environmental view of the portable and wearable disinfecting pouch of FIG. 1 being worn by a user with the user's hands inserted inside of the disinfecting pocket from both side opening for disinfecting the user's hands.

As shown in FIG. 2, one feature of portable and wearable disinfecting pouch 10 may be that it can be designed and configured to be worn around waist W of user U and used for disinfecting the hands 30, accessories 32, or items 34. As shown in FIG. 2, user U may insert their hands 30 inside of first opening 16, second opening 20, and or a combination thereof, into interior 24 of disinfecting pocket 14 for disinfecting and/or sanitizing their hands 30. As such, another feature of disclosed portable and wearable disinfecting pouch 10 may be that hands 30, accessories 32 or items 34 of user U (or others) can be sanitized by placing them inside disinfecting pocket 14 through first opening 16, second opening 20, and/or a combination thereof, and onto sanitizing pad 26 in interior 24 of disinfecting pocket 14.

As shown in the Figures, in select embodiments of portable and wearable disinfecting pouch 10, disinfecting pocket 14 may include back portion 36 and front cover portion 38. Back portion 36 may be positioned on waistbelt 12. Front cover portion 38 may be attached to back portion 36 on top side 40 and bottom side 42 of disinfecting pocket 14. This connection on top side 40 and bottom side 42 may create first opening 16 on first end 18 and second opening 20 on second end 22, with interior 24 therebetween. In select embodiments, first elastic band 44 and second elastic 52 band may be optionally included on first opening 16 and second opening 20, respectively. First elastic band 44 may be connected between first back side 46 of back portion 36 and first front side 48 of front cover portion 38. First elastic band 44 may be configured to provide first elastic opening 50 for first opening 16 on first end 18 of disinfecting pocket 14. Likewise, second elastic band 52 may be connected between second back side 54 of back portion 36 and second front side 56 of front cover portion 38. Second elastic band 52 may be configured to provide second elastic opening 58 for second opening 20 on second end 22 of disinfecting pocket 14.

Also shown in the Figures, another feature of portable and wearable disinfecting pouch 10 may be the inclusion of removable attachment 60. Removable attachment 60 may be for providing a means for easily accessing interior 24 of disinfecting pocket 14, like for filling sanitizing pad 26 with sanitizing formula 28, or the like, or for changing out sanitizing pad 26 and/or drying material 64. In select embodiments, removable attachment 60 may be on top side 40 of disinfecting pocket 14 between front cover portion 38 and back portion 36. Wherein, with removable attachment 60 on top side 40 of disinfecting pocket 14, interior 24 of disinfecting pocket 14 may be accessed by disengaging removable attachment 60 on top side 40 and folding down front cover portion 38. Removable attachment 60 may be any type of removable attachment between front cover portion 38 and back portion 36. In select embodiments, and clearly not limited thereto, removable attachment 60 on top side 40 of disinfecting pocket 14 may be zippered attachment 62, as shown in the Figures. However, the disclosure is clearly not limited thereto, and any similar removable attachment may be used. With zippered attachment 62, interior 24 of disinfecting pocket 14 may be accessed by unzipping zippered attachment 62 on top side 40 of disinfecting pocket 14 and folding down front cover portion 38, as shown in FIGS. 3-7.

Figure 10:
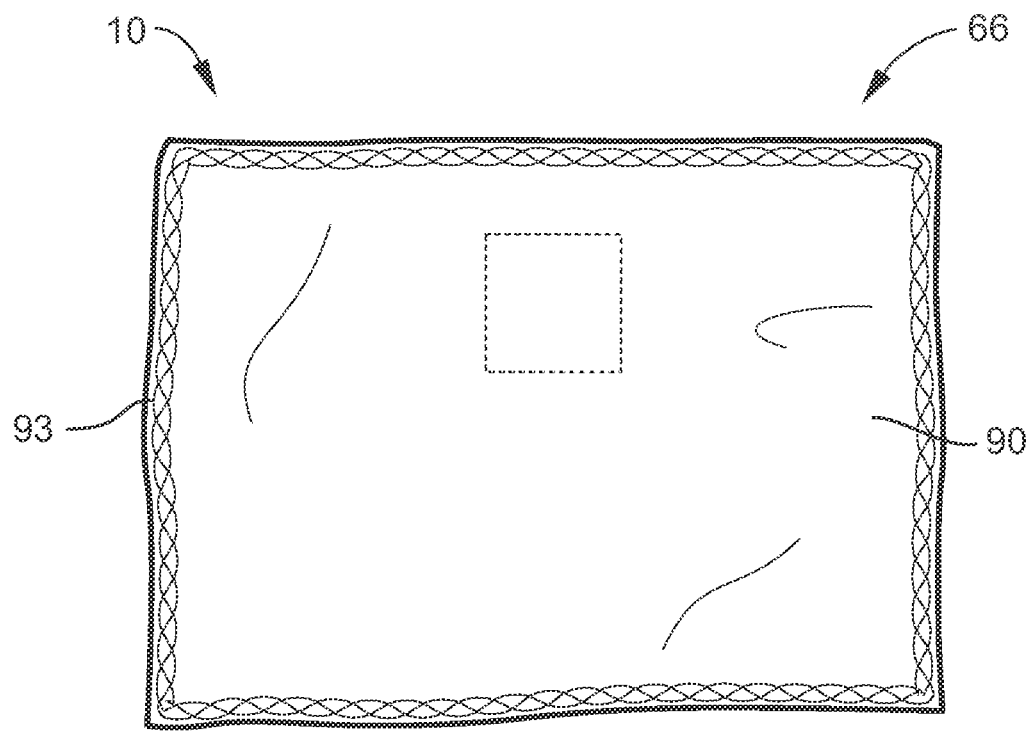
FIG. 10 is a front view of the drying material according to select embodiments of the instant disclosure for use in the portable and wearable disinfecting pouch.
Figure 11:
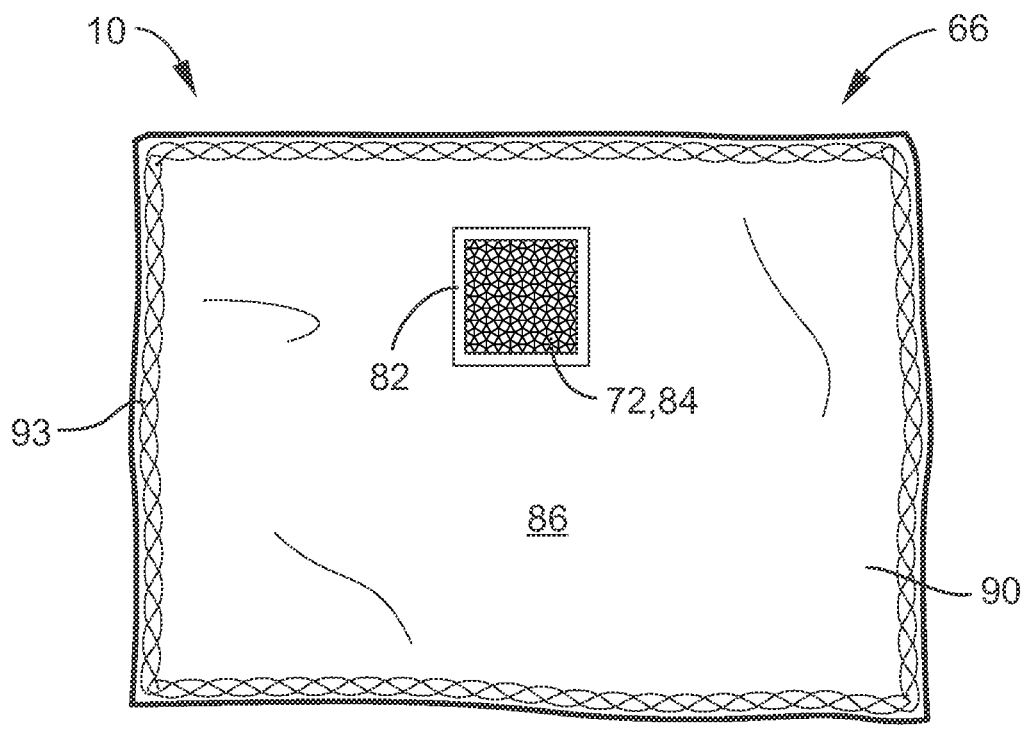
FIG. 11 is a back view of the drying material of FIG. 10.
Figure 12:
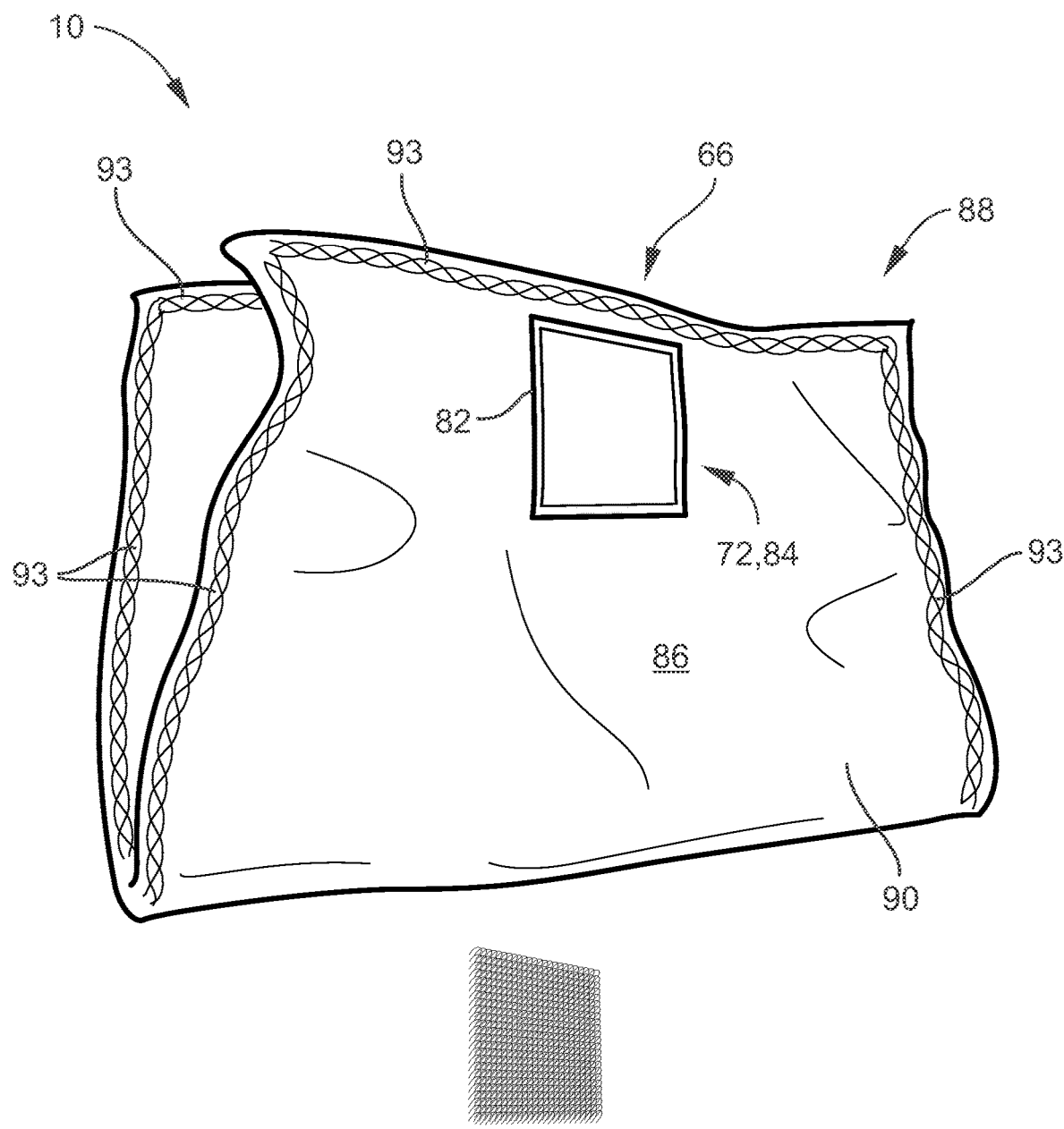
FIG. 12 is a back view of the drying material of FIG. 10 in a folded-up orientation for insertion into the disinfecting pocket of the disclosed portable and wearable disinfecting pouch.

Referring now to FIGS. 3-7 and 10-12, another feature of portable and wearable disinfecting pouch 10 may be that disinfecting pocket 14 may further include drying material 64. Drying material 64 may be configured for drying hands 30, accessories 32, items 34, or the like. Drying material may include any type of means or material configured for drying hands 30, accessories 32, items 34, or the like. In select embodiments of portable and wearable disinfecting pouch 10, drying material 64 may be, but is not limited to, antimicrobial fabric cloth 90. In select embodiments, antimicrobial fabric cloth 90 may include reinforced edges 93, like reinforced stitching or the like, like as best shown in FIGS. 10-12. In select embodiments, drying material 64 may be configured to be washable for multiple uses.

Figure 3:
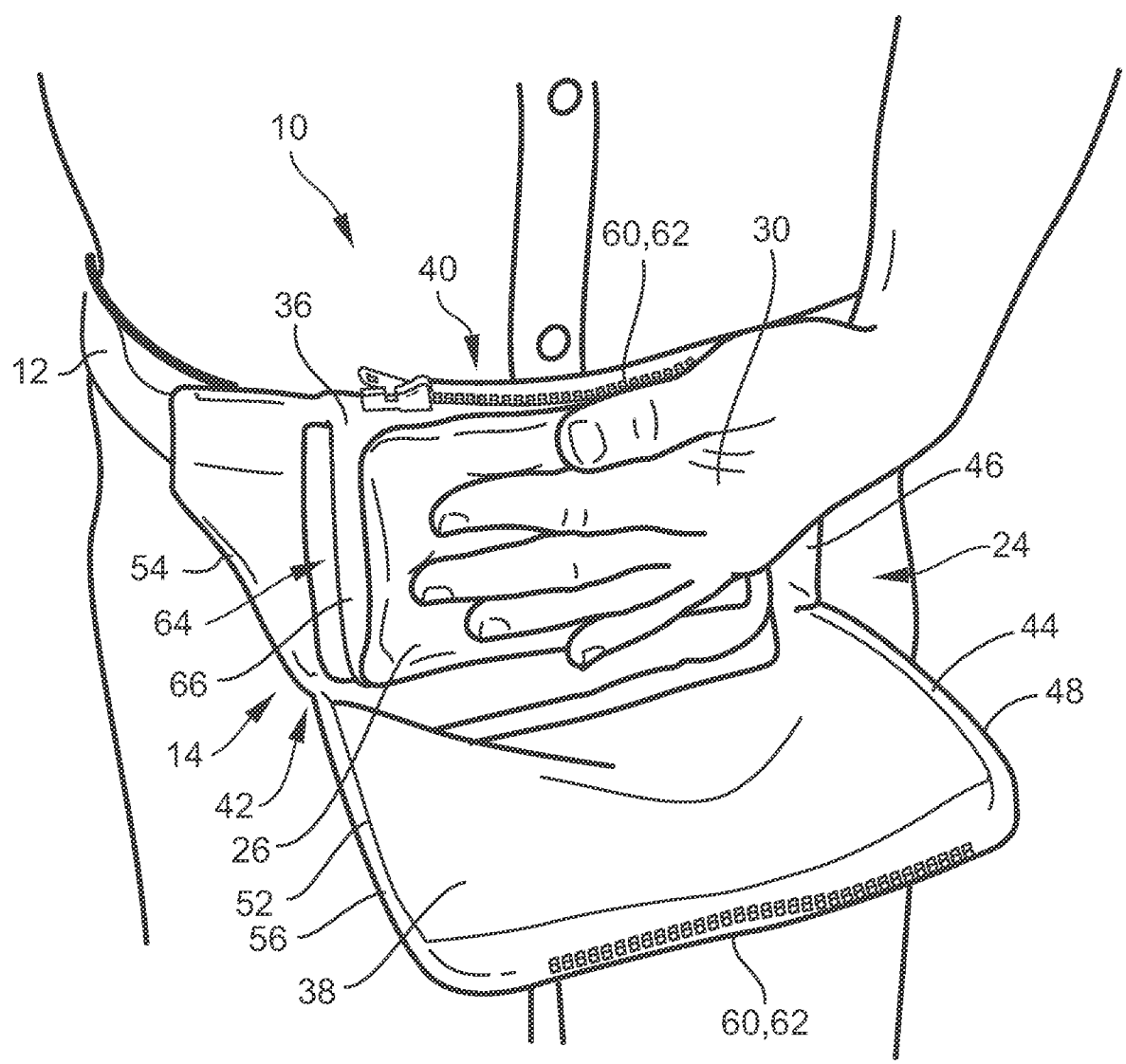
FIG. 3 is a left side, front perspective view of the portable and wearable disinfecting pouch of FIG. 1 with the zippered flap opened showing the inside of the disinfecting pocket.
Figure 4:
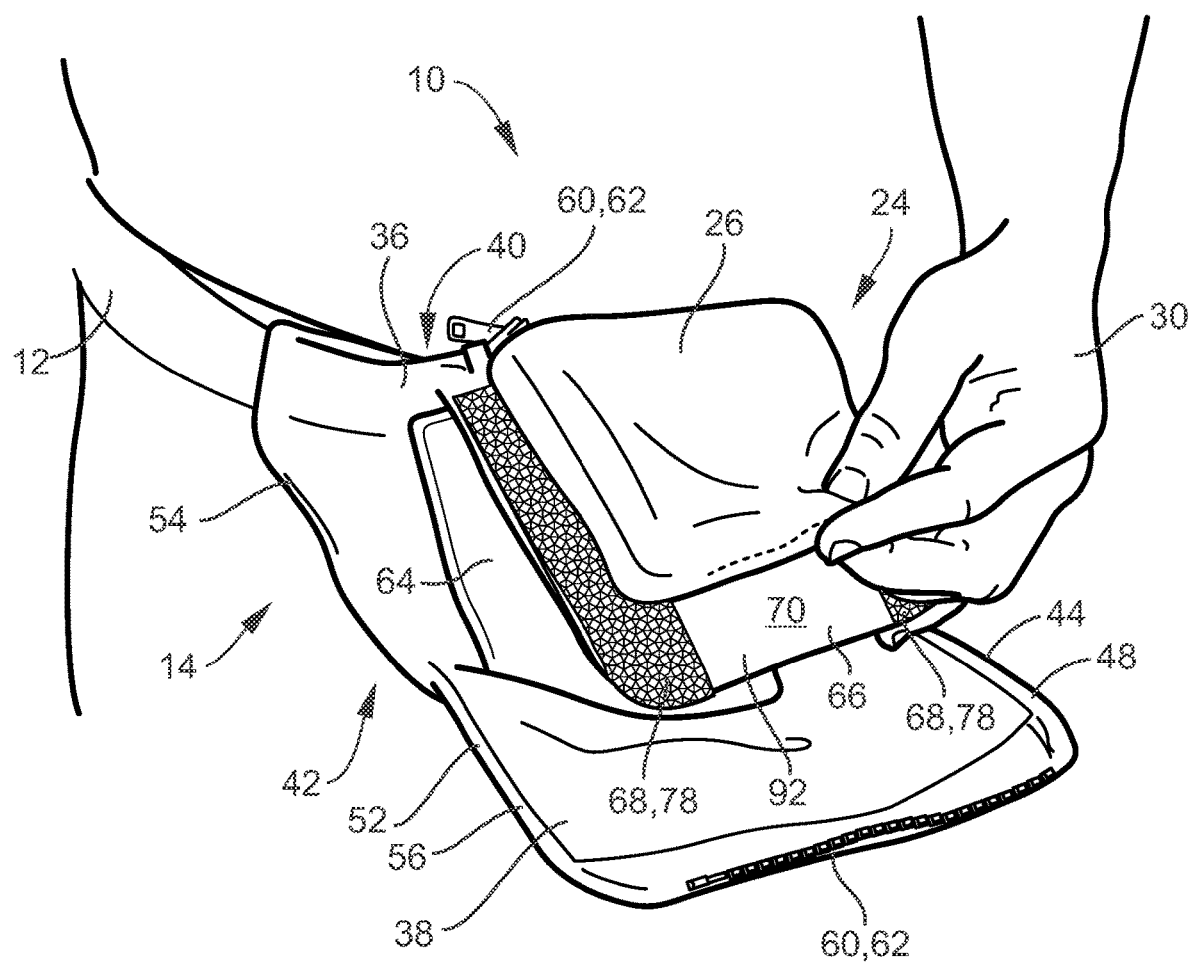
FIG. 4 is a left side, front perspective view of the portable and wearable disinfecting pouch of FIG. 1 with the zippered flap opened showing the sanitizing pad, the drying material, and the divider flap.
Figure 5:
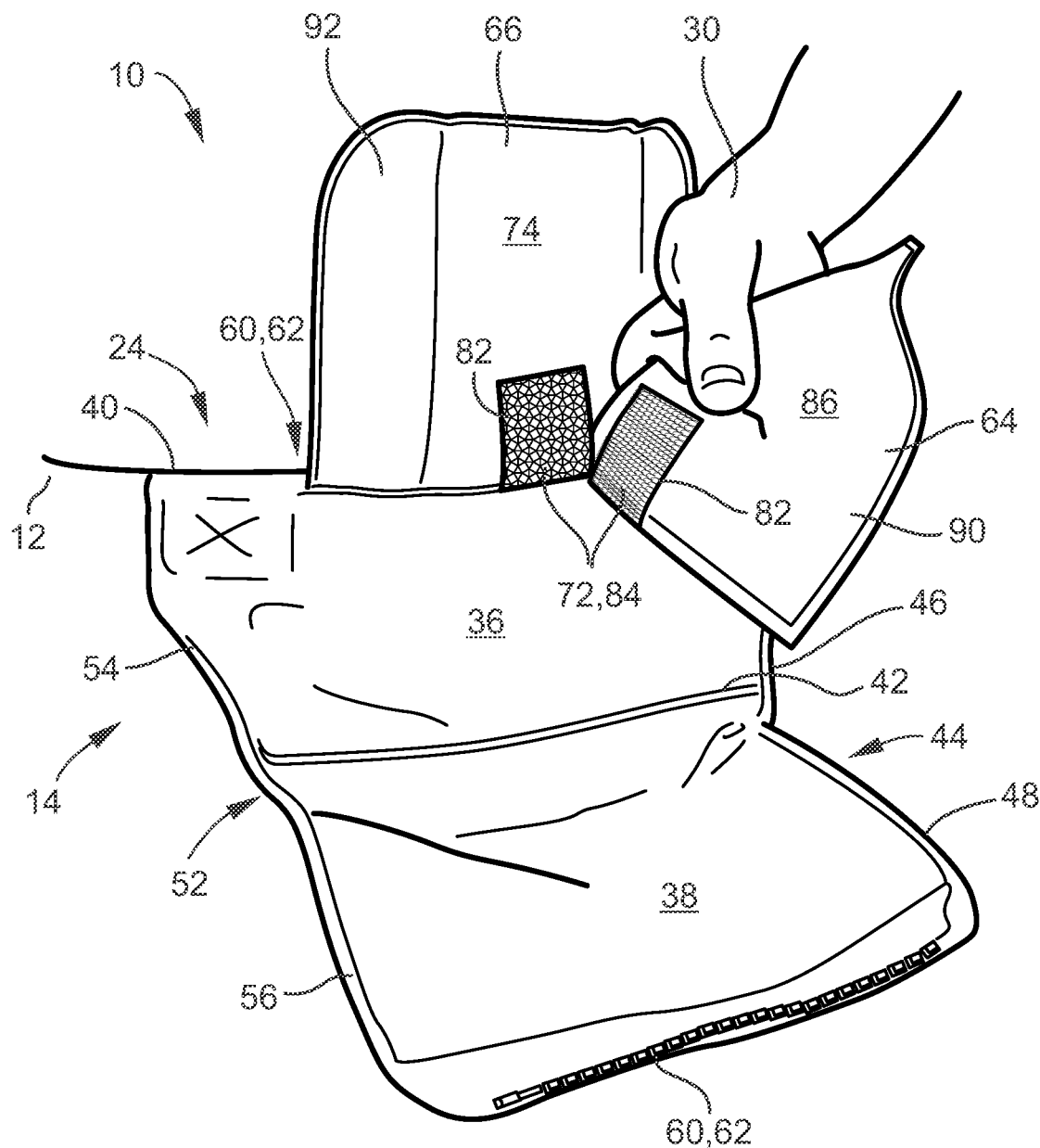
FIG. 5 is a left side, front perspective view of the portable and wearable disinfecting pouch of FIG. 1 with the zippered flap opened showing the divider flap lifted up and the drying material being removed from the back side of the divider flap.

Referring now to FIGS. 3-7, in select embodiments, divider flap 66 may be included in disinfecting pocket 14 of portable and wearable disinfecting pouch 10. Divider flap 66 may be positioned between drying material 64 and sanitizing pad 26. Divider flap 66 may be configured to prevent sanitizing formula 28 on sanitizing pad 26 from touching drying material 64. Divider flap 66 may be any material, means, or device for dividing drying material 64 from sanitizing pad 26. In select embodiments of portable and wearable disinfecting pouch 10, divider flap 66 may be, but is clearly not limited thereto, neoprene wall liner 92, as shown in the Figures. In select embodiments, divider flap 66 may include front side attachment means 68 (see FIGS. 4, 6, 7, and 9) configured to attach sanitizing pad 26 to front side 70 of divider flap 66 in interior 24 of disinfecting pocket 14. Front side attachment means 68 of divider flap 66 may include, but is not limited thereto, two vertical strips 76 of front side hook and loop type fastener 78 configured to removably attach to back sanitizing side 80 of sanitizing pad 26 for removably attaching sanitizing pad 26 to divider flap 66. In other select embodiments, divider flap 66 may include back side attachment means 72 (see FIGS. 5, 11 and 12) configured to attach drying material 64 to back side 74 of divider flap 66 in interior 24 of disinfecting pocket 14. Back side attachment means 72 of divider flap 66 may include, but is clearly not limited to, center strip 82 of back side hook and loop type fastener 84 configured to removably attach to front drying side 86 of drying material 64 for removably attaching drying material 64 to divider flap 66. Referring now to FIGS. 3 and 12, in select embodiments, and clearly not limited thereto, drying material 64 may be configured and sized to be attached to divider flap 66 in folded-up orientation 88 for allowing hands 30, accessories 32, items 34, and/or the like, to be inserted into disinfecting pocket 14 and between drying material 64 in folded-up orientation 88. In select embodiments, divider flap 66 may be attached to back portion 36 of disinfecting pocket 14 on top side 40, where divider flap 66 may be configured to fold upwards and out of disinfecting pocket 14 when it is opened for removing or attaching drying material 64 (see FIG. 5).

Referring again to FIG. 2, hands 30, accessories 32, items 34, or the like, of user U (or others) can be sanitized by placing them inside disinfecting pocket 14 through first opening 16, second opening 20, or a combination thereof, and onto sanitizing pad 26 in interior 24 of disinfecting pocket 14, and hands 30, accessories 32, items 34, or the like of user U (or others) can then be dried after they are sanitized by placing them inside disinfecting pocket 14 through first opening 16, second opening 20, or the combination thereof, and onto drying material 64 in interior 24 of disinfecting pocket 14.

Figure 6:
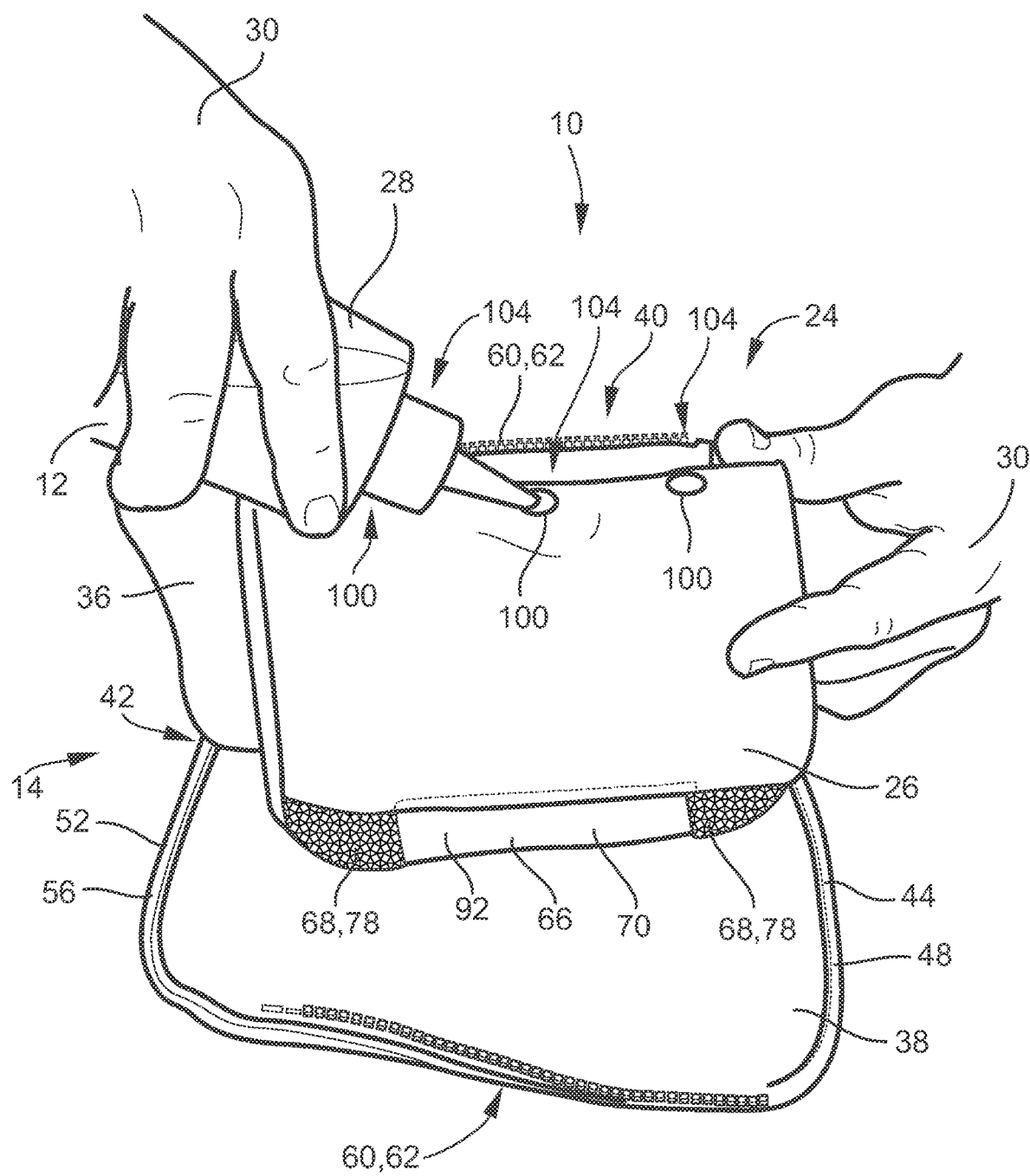
FIG. 6 is a top, front perspective view of the portable and wearable disinfecting pouch of FIG. 1 with the zippered flap opened showing the sanitized pad being filled with the sanitizing formula.
Figure 7:
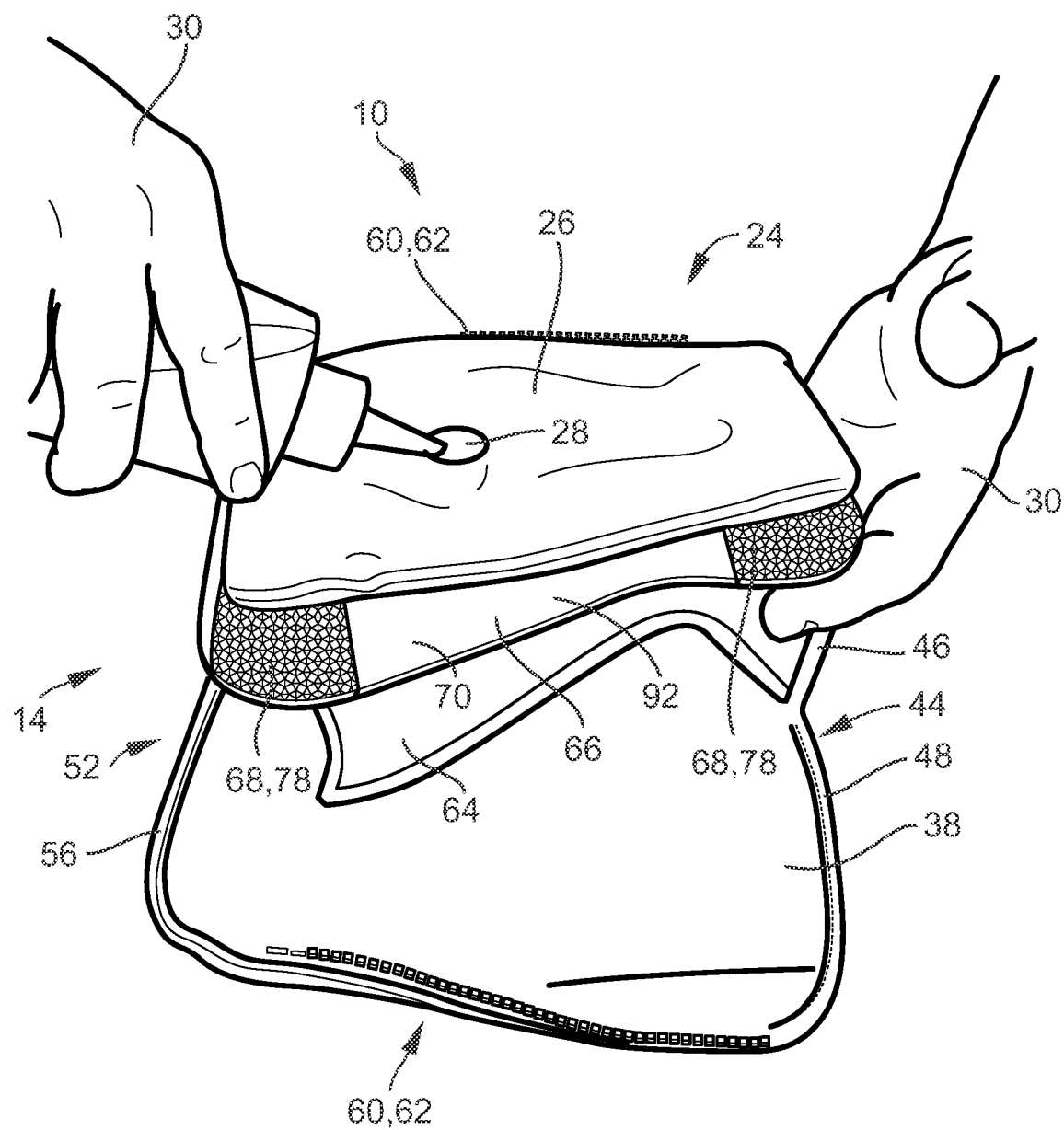
FIG. 7 is a top, perspective view of the portable and wearable disinfecting pouch of FIG. 1 with the zippered flap opened showing the sanitized pad being coated with the sanitizing formula.
Figure 8:
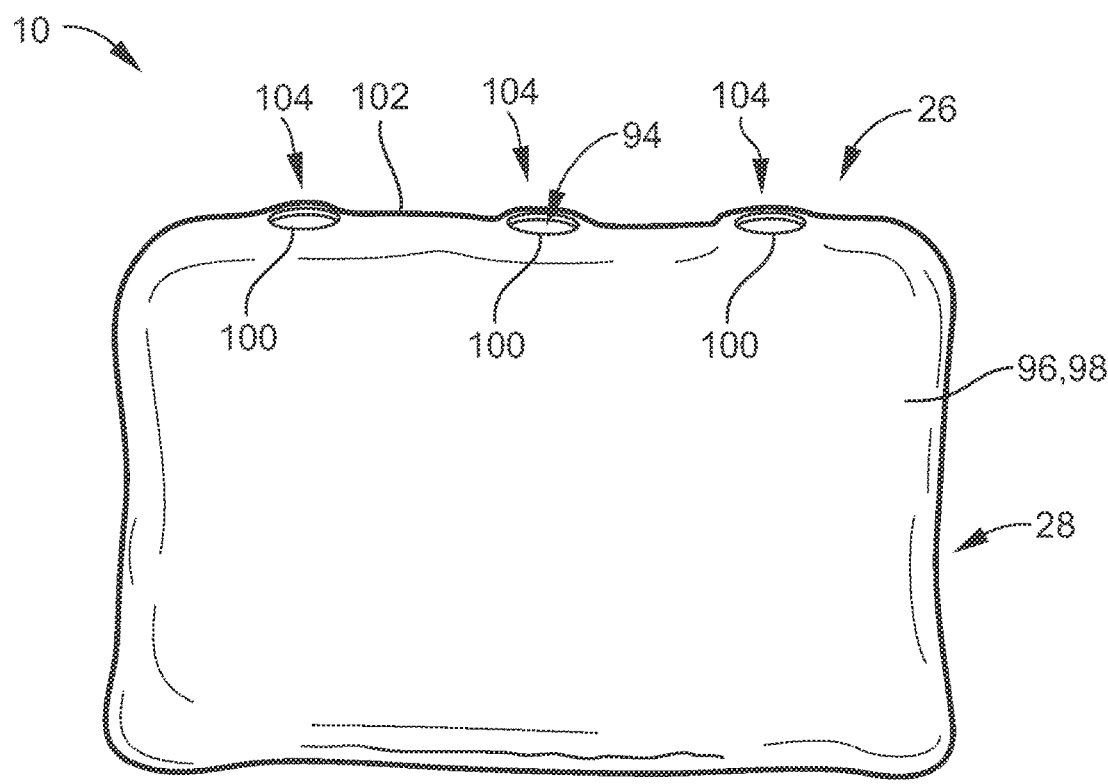
FIG. 8 is a front view of the sanitizing pad according to select embodiments of the instant disclosure for use in the portable and wearable disinfecting pouch.
Figure 9:
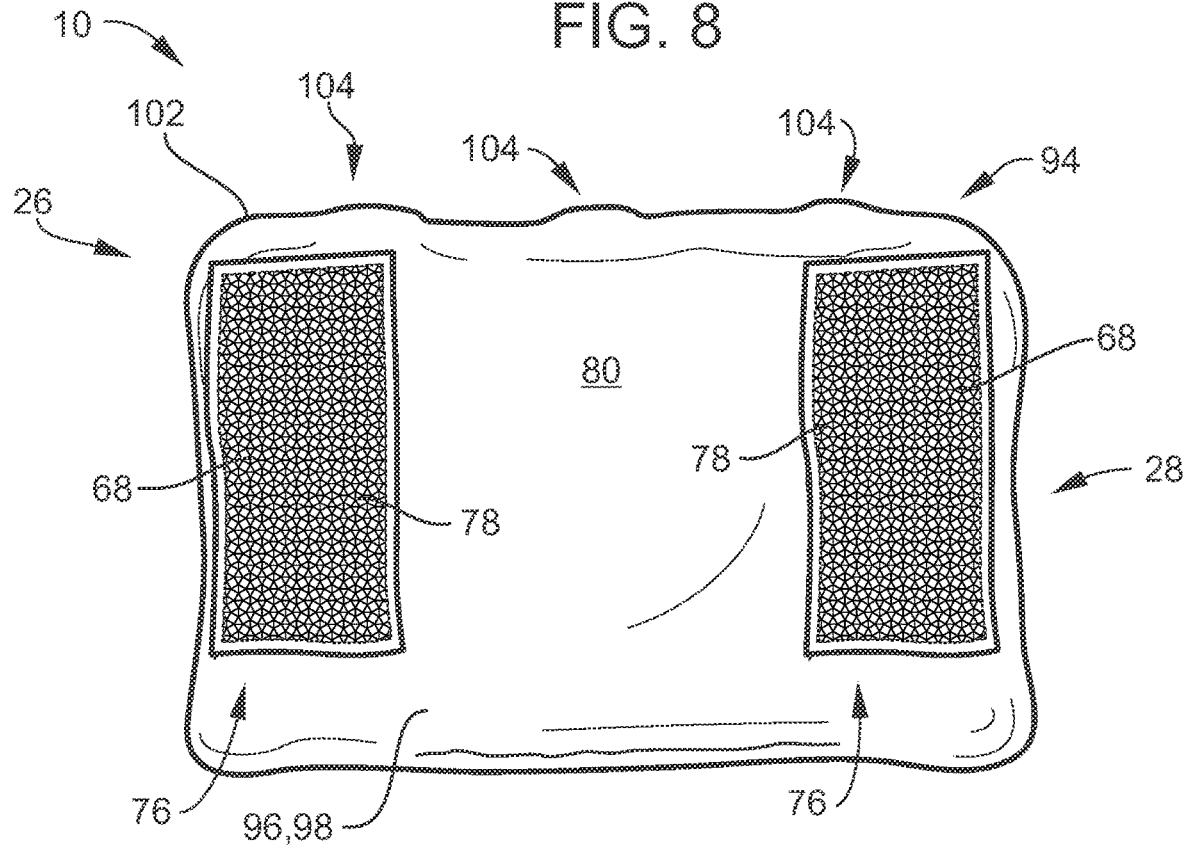
FIG. 9 is a back view of the sanitizing pad of FIG. 8.

Referring now specifically to FIGS. 6, 8 and 9, in select embodiments of portable and wearable disinfecting pouch 10, sanitizing pad 26 may include, but is not limited thereto, absorbent foam interior 94 and antimicrobial fabric exterior 96. However, the disclosure is not limited thereto, and any various materials may be included for sanitizing pad 26 designed to hold sanitizing liquid 28 or the like. Antimicrobial fabric exterior 96 may surround absorbent foam interior 94. In select possibly preferred embodiments, antimicrobial fabric exterior 96 may include, but is not limited to, silver-ion fabric material 98, which may be configured to eliminate the growth of any bacteria, or the like. In select embodiments, antimicrobial fabric exterior 96 of sanitizing pad 26 may include at least one filling hole 100 therethrough. Each of the at least one filling holes 100 may be configured for inserting sanitizing formula 28 inside of sanitizing pad 26 and onto absorbent foam interior 94, like as shown in FIG. 6. In select embodiments, antimicrobial fabric exterior 96 of sanitizing pad 26 may include, but is not limited thereto, three filling holes 100 therethrough. The three filling holes 100 may be positioned along top edge 102 of sanitizing pad 26. The three filling holes 100 may be configured for inserting sanitizing formula 28 inside of sanitizing pad 26 and onto absorbent foam interior 94 in three filling locations 104. However, the disclosure is not so limited, and any desired number of filling holes 100 may be included for providing any number of filling locations 104. Another feature of antimicrobial fabric exterior 96 may be that sanitizing liquid 28 may be sprayed or coated on the outside of sanitizing pad 26, like as shown in FIG. 7, where sanitizing liquid 28 may absorb into antimicrobial fabric exterior 96. In select embodiments, sanitizing pad 26 may be configured to be washable for multiple uses.

Referring now back to FIG. 1, another feature of portable and wearable disinfecting pouch 10 may be that, in select embodiments, front accessories pocket 106 and/or back accessories pocket 107 may be included. Front accessories pocket 106 may be positioned on front cover portion 38 of disinfecting pocket 14. Back accessories pocket 107 may be positioned on back portion 35 of disinfecting pocket 14. Front accessories pocket 106 and/or back accessories pocket 107 may be configured for holding accessories 32, items 34, or the like. As shown in FIG. 1, front accessories pocket 106 and/or back accessories pocket 107 may include, but is not limited to, a zippered opening or the like, or just a slotted opening, configured for concealing the contents inside of front accessories pocket 106 and/or back accessories pocket 107.

Still referring back to FIG. 1, another feature of portable and wearable disinfecting pouch 10 may be that in select embodiments at least one side apron 108 may be included. Each of the at least one side aprons 108 may be positioned along waistbelt 12. Each of the at least one side aprons 108 may be configured with slots 110 for holding accessories 32, items 34, or the like. In select embodiments, and clearly not limited thereto, two side aprons 108 may be included on each side of disinfecting pocket 14 on waistbelt 12.

In another aspect, the instant disclosure embraces portable and wearable disinfecting pouch 10 in any embodiment and/or combination of embodiments shown and/or described herein.

Figure 13:
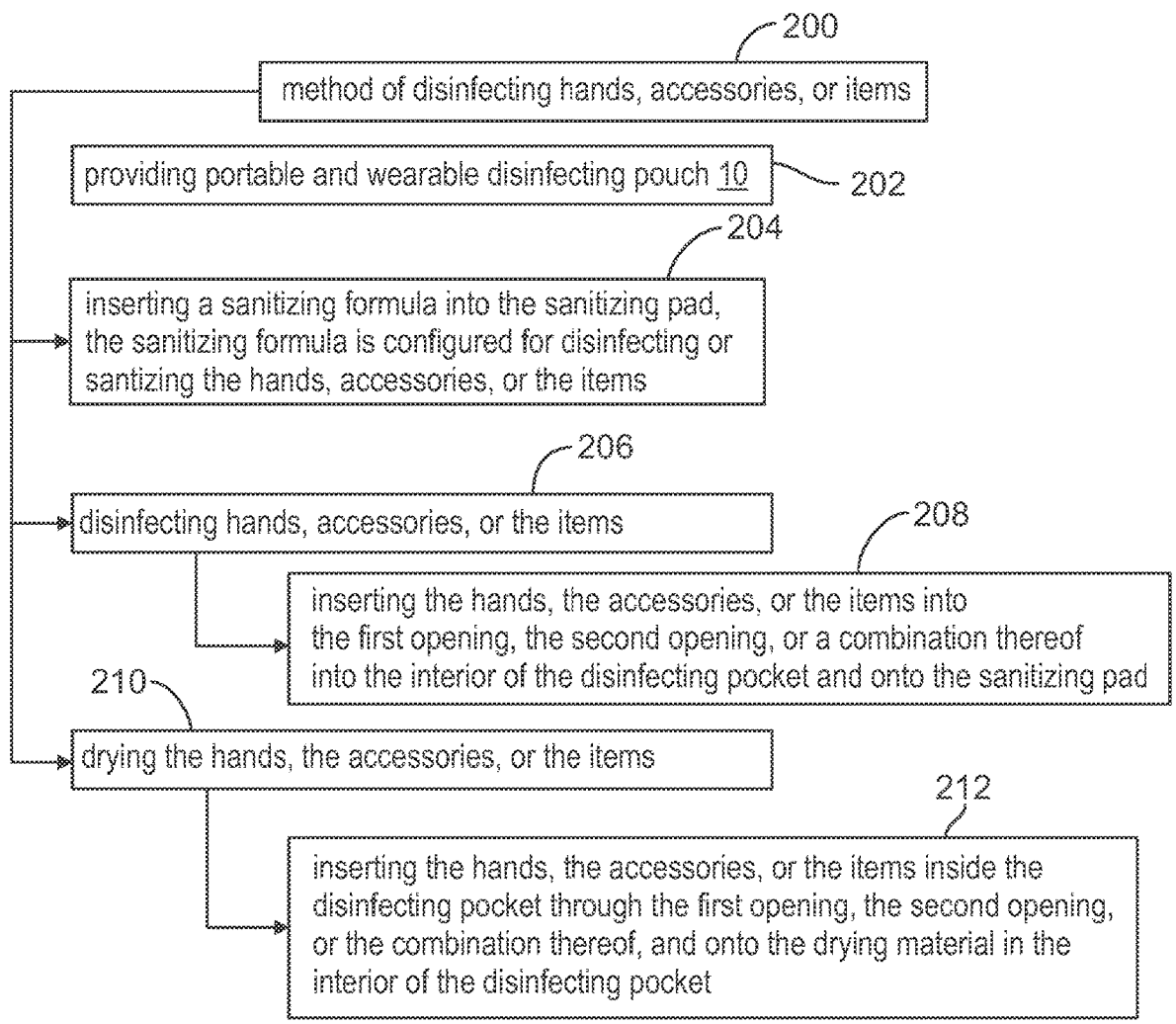
FIG. 13 is a flow chart of the method of disinfecting hands, accessories, or items according to select embodiments of the instant disclosure.

Referring now to FIG. 13, in another aspect, the instant disclosure embraces method 200 of disinfecting hands 30, accessories 32, or items 34. Method 200 of disinfecting hands 30, accessories 32, or items 34 may generally include utilizing portable and wearable disinfecting pouch 10 in any embodiment and/or combination of embodiments shown and/or described herein. As such, in general, method 200 of disinfecting hands 30, accessories 32, or items 34 may include step 202 of providing portable and wearable disinfecting pouch 10 in any embodiment and/or combination of embodiments shown and/or described herein. With the provided portable and wearable disinfecting pouch 10, method 200 of disinfecting hands 30, accessories 32, or items 34 may further include the steps of: step 204 of inserting sanitizing formula 28 into sanitizing pad 26 (see FIGS. 6 and 7), where sanitizing formula 28 is configured for disinfecting or sanitizing hands 30, accessories 32, or items 34; and step 206 of disinfecting hands 30, accessories 32, or items 34 including step 208 of inserting hands 30, accessories 32, or items 34 into first opening 16, second opening 20, or a combination thereof, into interior 24 of disinfecting pocket 14 and onto sanitizing pad 26.

Still referring to FIG. 13, in select embodiments of embraces method 200 of disinfecting hands 30, accessories 32, or items 34, when the provided portable and wearable disinfecting pouch 10 further includes drying material 64 inside of disinfecting pocket 14, method 200 of disinfecting hands 30, accessories 32, or items 34 may further include step 210 of drying hands 30, accessories 32 or items 34 after they are disinfected by step 212 of inserting them inside disinfecting pocket 14 through first opening 16, second opening 20, or the combination thereof, and onto drying material 64 in interior 24 of disinfecting pocket 14.

FIG. 2 shows a view of portable and wearable disinfecting pouch 10 as it would be seen worn on waist W of user U. Accessories pocket 106 is shown with a zippered closure front and center. Accessories pocket 106 may be an area for holding accessories, as in a cell phone or keys. At the top of portable and wearable disinfecting pouch 10 you can see the larger zippered attachment 62, which when closed (as in the illustration), shows the product ready to be used. On both the right and left side is a representation of waistbelt 12 that is attached to the main framework of the device, which holds disinfecting pocket 14 on waist W of user U and has a strap extension and buckle connector 13 for adjusting the size of waistbelt 12. Beneath zippered attachment 62 and where the main framework of disinfecting pocket 14 begins, on each side is first and second elastic band openings (50 and 58), which are designed and configured to keep interior 24 of disinfecting pocket 14 moisture secured.

Referring to FIGS. 3-7, visual representations of when disinfecting pocket 14 is opened up by zippered attachment 62 at top side 40. As you open disinfecting pocket 14, interior 24 of the device is revealed. Portable and wearable disinfecting pouch 10 may be designed with the utility of wiping hands and accessories onto sanitizing pad 26 within interior 24 of disinfecting pocket 14, to sanitize hands 30, accessories, 32, items, 34, or the like, with sanitizing formula 28 in sanitizing pad 26, while having drying material 64 for drying hands 30, accessories, 32, items, 34, or the like. As an example, sanitizing pad 26 may be made up of a polyurethane pad and an antimicrobial fabric. This entire pad system may be connected and can be removed by the fasteners (76, 78) connected to both sanitizing pad 26 and divider flap 66 in interior 24 of disinfecting pocket 14. As user U disinfects hands 30 (or other items), user U may simply flip the neoprene divider flap 66 forward, to access the dry antimicrobial fabric cloth 90 within the device. This antimicrobial fabric cloth 90 may be fastened and can be removed (replaced) from neoprene divider flap 66. Fasteners (82, 84) may keep antimicrobial fabric cloth 90 in place and offer a drying station for hands and accessories. Zipper attachment 62 is shown at the bottom from being opened up and flipped down. The device allows for easy access to remove and replace sanitizing pad 26 and drying material 64.

In use, by buckling connector 13 of waistbelt 12 around waist W of user U, disinfecting pouch 10 may be easy and convenient to use throughout the day. User U may simply place its hands into disinfecting pocket 14 and onto sanitizing pad 26 to kill and inactivate viruses, pathogens and bacteria. After placing its hands into the disinfecting area, user U may use its fingers to slide the divider flap 66 forward to access the dry antimicrobial fabric cloth 90 and dry its hands. As seen on top side 40 of disinfecting pocket 14, zipper attachment 62 can be unzipped to open disinfecting pocket 14 for replacing sanitizing pad 26 and/or drying material 64. After replacing, user U may simply zip back shut zipper attachment 62 and the device is ready for use. Portable and wearable disinfecting pouch 10 may give user U the confidence to navigate into public, touching things, knowing it has disinfecting pouch 10 ready to use after all its inconspicuous touching. As seen in FIGS. 6-7, sanitizer formula 28 may be filled into the antimicrobial sanitizing pad 26. This pad may holds as much as 8 ounces of sanitizing solution and may act as a dispenser within the pouch. Sanitizing pad 26 may be designed to use a bottle of sanitizer and pour its contents into the specifically design filling holes 100 at top edge 102 (see FIG. 6). In addition, some sanitizer formula 28 should be poured on the front of sanitizing pad 26 (see FIG. 7). When more sanitizer formula 28 is needed, absorbent foam interior 94 within sanitizing pad 26 may be refilled by the designed filling holes 100. A container (like the one the product is provided in) can also be used to dip sanitizing pad 26 into, like a tray of sanitizing formula 28. Sanitizing pad 26 can be removed and replaced each day and may be washable. In select embodiments, sanitizing pad 26 may have a neoprene/waterproof backing (divider flap 66) and can be built with antimicrobial, silver-ion fabric material 98, to eliminate the growth of bacteria. Sanitizing pad. 26 may also be disposable, whereby you can simply place one of the disposable sanitizing pads 26 into disinfecting pocket 14, onto the fasteners of the divider flap 66, and throw it away at the end of its use. Disposables may be meant for one day use only.

In sum, as seen in the image, portable and wearable disinfecting pouch 10 may be worn on the human body and may be designed to allow for an easy to use, quick option to disinfect your hands or other accessories or items. The disclosed portable and wearable disinfecting pouch 10 may be designed and created to help people gain confidence navigating back into public by having a mobile disinfecting pouch on them at all times. A feature of the present disclosure may be its ability to be worn on the body. Another feature of the present disclosure may be its ability to have hands-free access to sanitized hands and accessories. Another feature of the present disclosure may be its ability to sanitize and dry hands throughout the day whenever necessary.

In the specification and/or figures, typical embodiments of the disclosure have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The foregoing description and drawings comprise illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Accordingly, the present disclosure is not limited to the specific embodiments illustrated herein but is limited only by the following claims.

The invention claimed is:

1. A portable and wearable disinfecting pouch comprising:
 a waistbelt;
 a disinfecting pocket positioned on the waistbelt, the disinfecting pocket including:
  a first opening on a first end of the disinfecting pocket;
  a second opening on a second end of the disinfecting pocket;
  an interior positioned between the first opening and the second opening; and
  a sanitizing pad positioned in the interior of the disinfecting pocket, the sanitizing pad containing a sanitizing formula configured for disinfecting or sanitizing hands, accessories, or items, wherein the sanitizing pad including:
   an absorbent foam interior; and
   an antimicrobial fabric exterior surrounding the absorbent foam interior, the antimicrobial fabric exterior including a silver-ion fabric material configured to eliminate growth of bacteria.

2. The portable and wearable disinfecting pouch of claim 1 being designed and configured to be worn around a waist of a user and used for disinfecting the hands, the accessories, or the items.

3. The portable and wearable disinfecting pouch of claim 2, whereby the disinfecting pocket is configured to sanitize the hands, the accessories or the items of the user by placing the hands, the accessories, or the items inside the disinfecting pocket through the first opening, the second opening, or a combination thereof, and onto the sanitizing pad in the interior of the disinfecting pocket.

4. The portable and wearable disinfecting pouch of claim 1, wherein the disinfecting pocket including:
 a back portion positioned on the waistbelt;
 a front cover portion attached to the back portion on a top side and a bottom side of the disinfecting pocket
 a first elastic band connected between a first back side of the back portion and a first front side of the front cover portion, the first elastic band is configured to provide a first elastic opening for the first opening on the first end of the disinfecting pocket; and
 a second elastic band connected between a second back side of the back portion and a second front side of the front cover portion, the second elastic band is configured to provide a second elastic opening for the second opening on the second end of the disinfecting pocket.

5. The portable and wearable disinfecting pouch of claim 4, wherein the disinfecting pocket including a removable attachment on the top side between the front cover portion and the back portion, wherein the interior of the disinfecting pocket may be accessed by disengaging the removable attachment on the top side and folding down the front cover portion.

6. The portable and wearable disinfecting pouch of claim 5, wherein the removable attachment on the top side of the disinfecting pocket is a zippered attachment, wherein the interior of the disinfecting pocket may be accessed by unzipping the zippered attachment on the top side of the disinfecting pocket and folding down the front cover portion.

7. The portable and wearable disinfecting pouch of claim 1, wherein the disinfecting pocket further including:
 a drying material configured for drying the hands, the accessories, or the items; and
 a divider flap positioned between the drying material and the sanitizing pad, the divider flap is configured to prevent the sanitizing formula on the sanitizing pad from touching the drying material.

8. The portable and wearable disinfecting pouch of claim 7, whereby:
 the disinfecting pocket is configured to sanitize the hands, the accessories or the items of a user by placing the hands, the accessories, or the items inside the disinfecting pocket through the first opening, the second opening, or a combination thereof, and onto the sanitizing pad in the interior of the disinfecting pocket; and
 the drying material is configured to dry the hands, the accessories or the items of the user after they are sanitized by placing the hands, the accessories, or the items inside the disinfecting pocket through the first opening, the second opening, or the combination thereof, and onto the drying material in the interior of the disinfecting pocket.

9. The portable and wearable disinfecting pouch of claim 7, wherein:
 the divider flap including a front side attachment means configured to attach the sanitizing pad to a front side of the divider flap in the interior of the disinfecting pocket; and
 the divider flap including a back side attachment means configured to attach the drying material to a back side of the divider flap in the interior of the disinfecting pocket.

10. The portable and wearable disinfecting pouch of claim 9, wherein:
 the front side attachment means of the divider flap including two vertical strips of a front side hook and loop type fastener configured to removably attach to a back sanitizing side of the sanitizing pad for removably attaching the sanitizing pad to the front side of the divider flap;
 the back side attachment means of the divider flap including a center strip of a back side hook and loop type fastener configured to removably attach to a front drying side of the drying material for removably attaching the drying material to the back side of the divider flap; and
 where, the drying material is configured and sized to be attached to the divider flap in a folded-up orientation for allowing the hands, the accessories, or the items to be inserted into the disinfecting pocket and between the drying material in the folded-up orientation.

11. The portable and wearable disinfecting pouch of claim 9, wherein the divider flap is attached to a back portion of the disinfecting pocket on a top side, where the divider flap is configured to fold upwards and out of the disinfecting pocket when it is opened for removing or attaching the drying material.

12. The portable and wearable disinfecting pouch of claim 7, wherein the drying material is an antimicrobial fabric cloth with reinforced edges, and the divider flap is a neoprene wall liner.

13. The portable and wearable disinfecting pouch of claim 1 further comprising at least one side apron positioned along the waistbelt, the side apron is configured with slots for holding the accessories or the items.

14. The portable and wearable disinfecting pouch of claim 1, wherein the antimicrobial fabric exterior of the sanitizing pad including at least one filling hole therethrough configured for inserting the sanitizing formula inside of the sanitizing pad and onto the absorbent foam interior.

15. The portable and wearable disinfecting pouch of claim 14, wherein the antimicrobial fabric exterior of the sanitizing pad including three of the filling holes along a top edge of the sanitizing pad configured for inserting the sanitizing formula inside of the sanitizing pad and onto the absorbent foam interior in three filling locations.

16. The portable and wearable disinfecting pouch of claim 1 further comprising:
 a front accessories pocket positioned on a front cover portion of the disinfecting pocket, the front accessories pocket is configured for holding the accessories or the items;
 a back accessories pocket positioned on a back portion of the disinfecting pocket, the back accessories pocket is configured for holding the accessories or the items; or
 a combination thereof.

17. A portable and wearable disinfecting pouch designed and configured to be worn around a waist of a user and used for disinfecting hands, accessories, or items, the portable and wearable disinfecting pouch comprising:
 a waistbelt with a connector;
 a disinfecting pocket positioned on the waistbelt, the disinfecting pocket including:
  a first opening on a first end of the disinfecting pocket;
  a second opening on a second end of the disinfecting pocket;
  an interior positioned between the first opening and the second opening;
  a back portion positioned on the waistbelt;
  a front cover portion attached to the back portion on a top side and a bottom side of the disinfecting pocket
  a first elastic band connected between a first back side of the back portion and a first front side of the front cover portion, the first elastic band is configured to provide a first elastic opening for the first opening on the first end of the disinfecting pocket;
  a second elastic band connected between a second back side of the back portion and a second front side of the front cover portion, the second elastic band is configured to provide a second elastic opening for the second opening on the second end of the disinfecting pocket;
  a sanitizing pad positioned in the interior of the disinfecting pocket, the sanitizing pad containing a sanitizing formula configured for disinfecting or sanitizing the hands, the accessories, or the items, the sanitizing pad including an absorbent foam interior, and an antimicrobial fabric exterior surrounding the absorbent foam interior, the antimicrobial fabric exterior including a silver-ion fabric material configured to eliminate growth of bacteria, wherein the antimicrobial fabric exterior of the sanitizing pad including at least one filling hole therethrough configured for inserting the sanitizing formula inside of the sanitizing pad and onto the absorbent foam interior;
  a drying material configured for drying the hands, the accessories, or the items, the drying material is an antimicrobial fabric cloth with reinforced edges;
  a divider flap positioned between the drying material and the sanitizing pad, the divider flap is configured to prevent the sanitizing formula on the sanitizing pad from touching the drying material, the divider flap is a neoprene wall liner, the divider flap including:
   a front side attachment means configured to attach the sanitizing pad to a front side of the divider flap in the interior of the disinfecting pocket;
   a back side attachment means configured to attach the drying material to a back side of the divider flap in the interior of the disinfecting pocket;
   wherein the divider flap is attached to the back portion of the disinfecting pocket on the top side, where the divider flap is configured to fold upwards and out of the disinfecting pocket when it is opened for removing or attaching the drying material; and
  a removable attachment on the top side between the front cover portion and the back portion, wherein the interior of the disinfecting pocket may be accessed by disengaging the removable attachment on the top side and folding down the front cover portion;
 whereby:
  the disinfecting pocket is configured to sanitize the hands, the accessories or the items of the user by placing the hands, the accessories, or the items inside the disinfecting pocket through the first opening, the second opening, or a combination thereof, and onto the sanitizing pad in the interior of the disinfecting pocket; and
  the drying material is configured to dry the hands, the accessories or the items of the user after being sanitized by placing the hands, the accessories, or the items inside the disinfecting pocket through the first opening, the second opening, or
  the combination thereof, and onto the drying material in the interior of the disinfecting pocket.

18. A method of disinfecting hands, accessories, or items comprising:
 providing a portable and wearable disinfecting pouch comprising:
  a waistbelt;
  a disinfecting pocket positioned on the waistbelt, the disinfecting pocket including:
  a first opening on a first end of the disinfecting pocket;
  a second opening on a second end of the disinfecting pocket;
  an interior positioned between the first opening and the second opening; and
  a sanitizing pad positioned in the interior of the disinfecting pocket, wherein the sanitizing pad including:
   an absorbent foam interior; and
   an antimicrobial fabric exterior surrounding the absorbent foam interior, the antimicrobial fabric exterior including a silver-ion fabric material configured to eliminate growth of bacteria;

inserting a sanitizing formula into the sanitizing pad, the sanitizing formula is configured for disinfecting or sanitizing the hands, the accessories, or the items; and disinfecting the hands, the accessories, or the items by inserting the hands, the accessories, or the items into the first opening, the second opening, or a combination thereof, into the interior of the disinfecting pocket and onto the sanitizing pad.

19. The method of claim 18, wherein the provided portable and wearable disinfecting pouch further comprising a drying material inside of the disinfecting pocket, wherein the method further comprising:

drying the hands, the accessories or the items after being disinfected by placing the hands, the accessories or the items inside the disinfecting pocket through the first opening, the second opening, or the combination thereof, and onto the drying material in the interior of the disinfecting pocket.

\* \* \* \* \*